(12) United States Patent
Favier et al.

(10) Patent No.: US 10,039,568 B2
(45) Date of Patent: Aug. 7, 2018

(54) DEVICE FOR GUIDING A MEDICAL NEEDLE

(71) Applicant: UNIVERSITE JOSEPH FOURIER—GRENOBLE 1, St. Martin D'heres (FR)

(72) Inventors: Denis Favier, Saint Martin D'uriage (FR); Thierry Alonso, Saint Ismier (FR); Gregory Chagnon, Detrier (FR); Yinong Liu, Nedlands (AU); Alexandre Moreau-Gaudry, Meylan (FR)

(73) Assignee: UNIVERSITE GRENOBLE ALPES, St. Martin D'Heres (FR)

( * ) Notice: Subject to any disclaimer, the term of this patent is extended or adjusted under 35 U.S.C. 154(b) by 152 days.

(21) Appl. No.: 14/352,678

(22) PCT Filed: Oct. 18, 2012

(86) PCT No.: PCT/EP2012/070651
§ 371 (c)(1),
(2) Date: Apr. 17, 2014

(87) PCT Pub. No.: WO2013/057189
PCT Pub. Date: Apr. 25, 2013

(65) Prior Publication Data
US 2014/0257203 A1     Sep. 11, 2014

(30) Foreign Application Priority Data

Oct. 18, 2011 (FR) .................................... 11 59387

(51) Int. Cl.
*A61M 5/32* (2006.01)
*A61B 17/34* (2006.01)
(Continued)

(52) U.S. Cl.
CPC ...... *A61B 17/3403* (2013.01); *A61B 10/0233* (2013.01); *A61B 17/06066* (2013.01);
(Continued)

(58) Field of Classification Search
CPC .......... A61B 10/0233; A61B 17/06066; A61B 17/3478; A61B 2017/00331;
(Continued)

(56) References Cited

U.S. PATENT DOCUMENTS 5,231,989 A     8/1993  Middleman et al.
5,584,821 A  *  12/1996  Hobbs ............... A61M 25/0043
                                                            138/140

(Continued)

FOREIGN PATENT DOCUMENTS

WO     WO 2006/065913 A1     6/2006
WO     WO 2007/056590 A1     5/2007
(Continued)

OTHER PUBLICATIONS

Webster, III, R.J., et al., "Nonholonomic Modeling of Needle Steering," *International Journal of Robotics Research*, vol. 25, No. 5-6, May-Jun. 2006, pp. 509-525.
(Continued)

*Primary Examiner* — Rebecca E Eisenberg
(74) *Attorney, Agent, or Firm* — Womble Bond Dickinson (US) LLP (57) ABSTRACT

The invention relates to a device for guiding a medical needle, including said medical needle (1) and an insert (2) that is rotatably, translatably, and slidably arranged in the needle (1), wherein said device is characterized in that the insert (2) has, in the free state thereof, a curved distal portion (21), and in that the needle has at least two regions (11, 12), the mechanical behaviors of which are different, wherein the mechanical behaviors of each region (11, 12) and of the
(Continued)

curved distal portion (21) of the insert are selected such that a movement of the insert (2) into the needle (1) causes a local deformation of the needle and/or of the insert. The invention also relates to a method for manufacturing said device.

11 Claims, 5 Drawing Sheets

(51) Int. Cl.
    *A61B 10/02*     (2006.01)
    *A61B 17/06*     (2006.01)
    *A61B 17/00*     (2006.01)

(52) U.S. Cl.
    CPC . *A61B 17/3478* (2013.01); *A61B 2017/00331* (2013.01); *A61B 2017/00526* (2013.01); *A61B 2017/00867* (2013.01); *A61B 2017/061* (2013.01); *A61B 2017/06095* (2013.01)

(58) Field of Classification Search
    CPC ........... A61B 2017/00526; A61B 2017/00867; A61B 2017/06095; A61B 2017/061
    See application file for complete search history.

(56) References Cited

U.S. PATENT DOCUMENTS

| | | | |
|---|---|---|---|
| 5,772,641 A * | 6/1998 | Wilson | A61M 25/0009 604/523 |
| 6,197,015 B1 * | 3/2001 | Wilson | A61M 25/005 156/158 |
| 6,997,947 B2 | 2/2006 | Walak et al. | |
| 2004/0133124 A1 | 7/2004 | Bates et al. | |
| 2004/0133168 A1 | 7/2004 | Salcudean et al. | |
| 2005/0149062 A1 * | 7/2005 | Carroll | A61B 17/3478 606/129 |
| 2008/0097347 A1 | 4/2008 | Arvanaghi | |
| 2009/0171271 A1 * | 7/2009 | Webster | A61B 17/3417 604/95.01 |
| 2009/0270676 A1 | 10/2009 | Sicvol | |
| 2011/0087257 A1 | 4/2011 | To et al. | |

FOREIGN PATENT DOCUMENTS

| | | |
|---|---|---|
| WO | WO 2007/059233 A2 | 5/2007 |
| WO | WO 2010/020591 A1 | 2/2010 |

OTHER PUBLICATIONS

Wedlick, T.R., et al., "Characterization of Pre-Curved Needles for Steering in Tissue," *31st Annual International Coenference of the IEEE EMBS*, Minneapolis, MN, USA, Sep. 2-6, 2009, pp. 1200-1203.

Sears, P., et al., "A Steerable Needle Technology Using Curved Concentric Tubes," *Proceedings of the 2006 IEEE/RSJ International Conference on Initelligent Robots and Systems (IROS)*, Beijing, China, Oct. 9-15, 2006, pp. 2850-2856.

Favier, D., et al., "Influence of Thermomechanical Processing on the Superelastic Properties of a Ni-Rich Nitinol Shape Memory Alloy," *Materials Science and Engineering A*, 429, 2006, pp. 130-136.

Bellouard, Y., et al. "Local Annealing of Complex Mechanical Devices: A New Approach for Developing Monolithic Micro-Devices," *Materials Science and Engineering*, A273-275, 1999, pp. 795-798.

* cited by examiner

DEVICE FOR GUIDING A MEDICAL NEEDLE

FIELD OF THE INVENTION

The present invention concerns a device for guiding a medical needle and a method for manufacturing such a device.

BACKGROUND OF THE INVENTION

Medical needles are frequently used during surgical procedures in living bodies, for the purpose for example of performing punctures, injections, biopsies, etc. in a target located inside the body.

A medical needle is an elongate hollow tubular body.

In general, the needle has one bevelled end to facilitate passing through the tissues.

Depending on the procedure, the target may be located at a depth of 2 to 40 cm underneath the patient's skin.

However, the pathway which may be taken by the needle as far as the target located inside the body is not necessarily linear.

It is possible that there may be obstacles between the point of insertion of the needle and the target.

Such obstacles may be bones (through which the needle is unable to pass), sensitive organs (which risk being damaged by the needle), etc.

Also, it has been shown that a needle, at the time it is inserted, is subject to deformations.

This bending of the bevelled end therefore affects the pathway of the needle; the true pathway being different from the pathway intended by the practitioner.

In this respect, reference can be made to the work by Webster et al., "Nonhlonmic modeling of needle steering", International Journal of Robotics Research, Sage Publications Ltd, 2006, 25, pp. 509-525.

The practitioner therefore seeks to steer the needle along a controlled pathway in relation to obstacles lying between the point of insertion and the target.

Guide devices intended to deform the needle so that it can bypass identified obstacles have therefore been developed.

Document WO 2010/020591 for example discloses a medical needle equipped with actuators attached to the outer surface of the needle or incorporated in the wall thereof via micro-manufacturing techniques.

Said actuators allow local stress to be applied to the needle so as to act on the curve of its distal end.

However the manufacturing of these miniature actuators remains difficult and costly.

Document US 2009/0270676 discloses a guiding device for a needle comprising an outer cannula of which a distal portion is able to be curved by a cable actuating system. The needle which is less rigid than the outer cannula conforms to the curve of the outer cannula as and when it advances therein and returns to a straight shape once its distal tip has reached past the distal end of the cannula.

The article by T. R. Wedlick et al., "Characterization of Pre-Curved Needles for Steering in Tissue", 31$^{st}$ Annual International Conference of the IEEE EMBS Minneapolis, 26 Sep. 2009 presents research into determination of the influence of the radius of curvature and angle of curvature on the pathway of a needle whose distal tip is pre-curved.

However the tip of said needle is permanently curved, which limits the possibilities of modifying the pathway in relation to obstacles to be avoided.

The article "A steerable Needle Technology Using Curved Concentric Tubes", P. Sears et al., Proceedings of the 2006 IEEE/RSJ International Conference on Intelligent Robots and Systems, Oct. 9-15, 2006, pp. 2850-2856, describes a telescopic medical needle formed of a plurality of curved concentric tubes which allows a three-dimensional pathway to be imparted to the needle inside the patient's body to avoid bones or sensitive organs.

Depending on the respective rigidity of the different tubes, the curve of the needle can be imposed by the curve of the most rigid tube or by the combination of curves of tubes of equivalent rigidity.

However, said tube arrangement modifies the general curve of the needle and does not act specifically on the curve of the distal tip.

In addition this construction, for a given inner diameter, has the effect of increasing the outer diameter of the needle.

Yet it is sought on the contrary to minimise the outer diameter of the needle to limit trauma suffered by the body and to facilitate postoperative management.

There therefore subsists a need to design a device for guiding a medical needle that does not lead to increasing the diameter of the needle, which is easy and low cost to manufacture and which allows at least a localised curve to be imparted to the needle and/the insert.

BRIEF DESCRIPTION OF THE INVENTION

According to the invention, there is proposed a device for guiding a medical needle, comprising said medical needle and an insert arranged slidably in translation and rotation in the needle, said device being characterized in that, in a free condition, the insert has a curved distal portion and in that the needle has at least two regions having differing mechanical behaviour, the mechanical behaviour of each of said regions and of the curved distal portion of the insert being chosen so that movement of the insert inside the needle imposes localised deformation of the needle and/or insert.

By « mechanical behaviour» is meant in the present text the relationship between the stress and strain of a material at a given temperature.

In the intended application, the temperature under consideration is advantageously the temperature of a human or animal body into which the needle is to be steered.

By « localised deformation» is meant a variation in the curve of only one part of the needle and/or insert.

As will be described below, at least one of these regions is formed by local heat or thermo-mechanical treatment of the needle.

According to one embodiment, the needle has at least two regions of different rigidity, at least one of said regions having greater rigidity than the curved portion of the insert.

According to one particular embodiment, said regions form adjacent portions of the needle along a longitudinal axis of the needle.

According to another embodiment, said regions are adjacent on the circumference of the distal portion of the needle.

Advantageously, the insert has a solid cylindrical shape of circular cross-section.

Particularly advantageously, the needle and the insert are in biocompatible materials that are elastic, elastoplastic or super-elastic at the temperature of the human body.

According to one preferred embodiment of the invention, the needle and/or insert are in a nickel-titanium alloy.

According to one particular embodiment of the invention, the needle and the insert are of constant thickness.

The outer diameter of the needle may be between 0.3 and 2 mm and the diameter of the insert may be between 0.1 and 1.8 mm.

According to one embodiment of the invention the needle, from its distal tip towards its proximal tip, has a first portion whose rigidity is greater than the rigidity of the curved portion of the insert and a second portion whose rigidity is smaller than the rigidity of the curved portion of the insert.

A further object concerns a method for manufacturing a guiding device for medical needle, said device comprising said medical needle and an insert arranged slidingly in translation and rotation in the needle, said method being characterized in that the needle and the insert are in biocompatible materials that are elastic, elastoplastic or superelastic at the temperature of the human body and which undergo localised heat and/or thermo-mechanical treatment to form:

on the insert, at least one curved distal portion;
on the needle at least two regions having different mechanical behaviour;
the mechanical behaviour of each of said regions of the needle and of the curved distal end of the insert being chosen so that movement of the insert inside the needle causes localised deformation of the needle and/or insert.

In particularly advantageous manner, the heat and/or thermo-mechanical treatment applied to the needle forms at least two regions of different rigidity, at least one of said portions having greater rigidity than the rigidity of the curved portion of the insert.

Preferably, said heat or thermo-mechanical treatment is performed in a neutral atmosphere.

According to one particular embodiment, said heat or thermo-mechanical treatment comprises local irradiation of the needle via laser.

BRIEF DESCRIPTION OF THE DRAWINGS

Other features and advantages of the invention will become apparent from the following detailed description with reference to the appended drawings in which.

DETAILED DESCRIPTION OF THE INVENTION

Guiding Device

Figure 1:
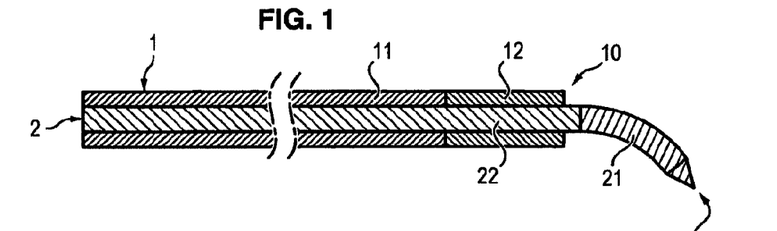
FIG. 1 is a cross-sectional view of the needle guiding device according to one embodiment of the invention.

With reference to FIG. 1, the device for guiding the medical needle comprises the needle itself 1 and an insert 2 adapted to slide in translation and rotation inside the needle 1.

The insert is of solid cylindrical shape with circular cross-section, whose diameter is slightly smaller than the inner diameter of the needle 1, so that it is able to slide inside the needle 1 without friction.

The needle 1 is of tubular shape with circular cross-section whose distal tip 10 (i.e. the end intended to pass through the tissues as far as the target) can be bevelled although the bevel cannot be seen in FIG. 1.

The needle may be of any size (length, inner and outer diameter) adapted in relation to the use for which it is intended.

For example, but not limited thereto, the inner diameter of the needle may typically be between 0.1 and 1.6 mm, its outer diameter may be between 1 and 1.8 mm, and its length may be between 3 and 40 cm.

The needle 1 and the insert 2 are made in materials adapted so that their behaviour changes under the effect of heat or thermo-mechanical treatment.

This makes it possible to manufacture the needle and the insert each in one same material over their entire length and subsequently to modify their mechanical behaviour locally—i.e. the curve for the insert—by means of heat or thermo-mechanical treatment.

Nickel-titanium alloys are known for their shape memory properties and are therefore particularly preferred for implementing the invention.

In particular, these alloys at the temperature of the human body have super-elastic properties enabling them to deform with great amplitude (in the order of 10%) in non-permanent manner.

In addition, they have the advantage of exhibiting very different properties depending on the heat treatments to which they are subjected, which offers a vast range of behaviours schematically illustrated in FIG. 3 and described in detail below.

However, depending on the applications of the device, it is possible to choose other suitable materials from the range of surgical stainless steels for the insert and/or needle, e.g. 316 L steel.

As can be seen in FIG. 1 the insert 2, when in a free condition (i.e. outside the needle), has a portion 21 adjacent to its distal end 20 which is curved.

Said curve is obtained by applying localised thermo-mechanical treatment to the distal end of the insert.

The remainder 22 of the insert is straight when the insert is in a free condition.

The distal end 20 of the insert preferably has an end-part of pyramidal, conical or even bevelled shape.

This end-part allows plugging of the inner diameter of the needle and thereby avoids a phenomenon of coring when the needle is inserted through the tissues.

Also, the needle 1 has at least two regions 11, 12 having different mechanical behaviour.

Said regions may be portions of the needle i.e. they extend over the entire circumference of the needle on a determined part of the length of the needle. These regions therefore lie adjacent along a longitudinal axis of the needle.

Alternatively, said regions may belong to one same portion of the needle each extending over part of the circumference of the needle.

The mechanical behaviour of the different regions 11, 12 of the needle and of portions 21, 22 of the insert is chosen so that, in relation to the position of the insert 2 inside the needle 1, it is possible to impose upon the needle 1 varying deformation of its distal tip and hence different pathways.

In the embodiment illustrated in FIG. 1, the region 11 corresponds to most of the length of the needle whilst the region 12 is the part of the needle adjacent the distal tip 10.

Advantageously, the length of the region 12 is of the order of the length of the curved portion 21 of the insert 2.

Figure 2A:
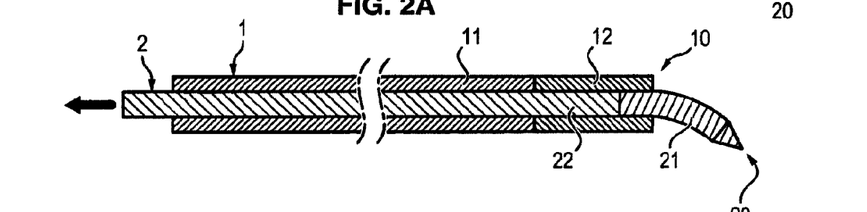
FIGS. 2A and 2B are cross-sectional views of the device in FIG. 1 according to different relative positions of the needle and the insert.
Figure 2B:
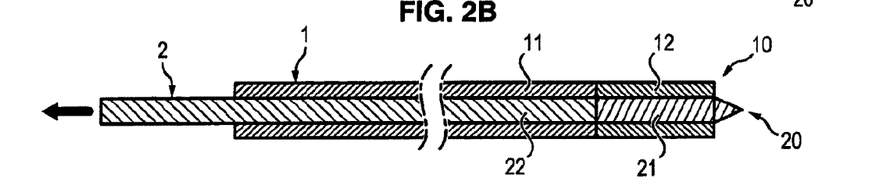

FIGS. 2A and 2B show two relative positions of the needle and the insert of the device in FIG. 1.

As illustrated in FIGS. 1 and 2A, when the curved portion 21 of the insert 2 projects (in full or in part) beyond the distal tip 10 of the needle, the needle 1 is straight.

When the needle is inserted, it is therefore the curved portion 21 of the insert 2 which chiefly imposes the pathway of the needle.

As illustrated in FIG. 2A, when the curved portion 21 is partly retracted inside the needle, the needle is almost straight i.e. in its region 12 it is more rigid than the curved portion 21 of the insert.

The curved part of the insert projecting beyond the distal tip 10, which is the effective guiding part, in this case has a less pronounced curve than when the entirety of the curved portion 21 of the insert projects beyond the distal tip 10 of the needle.

The practitioner is then able to impart upon the needle a pathway that has a more or less pronounced curve by moving the curved portion 21 of the insert to a greater or less extent out of the distal tip 10 of the needle.

As illustrated in FIG. 2B, when the distal end 20 of the insert 2 is positioned at the distal tip 10 of the needle 1, the curved portion 21 of the insert is surrounded by the region 12 of the needle 1.

The region 12 of the needle having greater rigidity than the curved portion 21 of the insert, it remains practically rectilinear.

The pathway of the needle in this configuration is therefore a straight line.

Judicious choice of the mechanical behaviours of the region 12 of the needle and of the curved portion 21 of the insert, which are obtained by means of localised heat or thermo-mechanical treatment of the needle and the insert, therefore allows the desired curve to be obtained as a function of the axial position of the insert 2 in relation to the needle 1.

Figure 3:
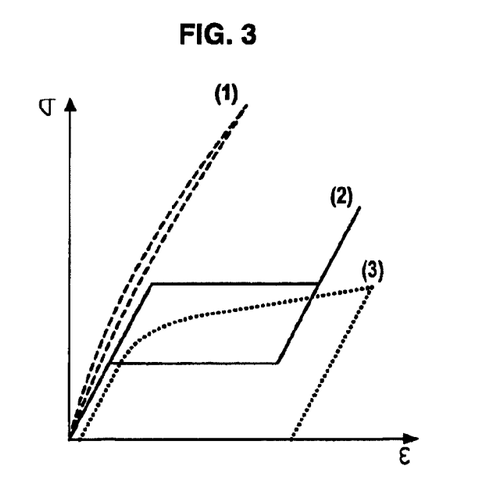
FIG. 3 gives stress-strain curves which can be chosen for the different regions of the insert and needle.

FIG. 3 gives behaviour curves (stress σ (in MPa) in relation to strain ε (in %)) that can be chosen for different portions of the insert and needle.

In well-known manner, these curves are plotted by means of tensile tests on a normalised test-piece made of the material under consideration.

Curve (1) corresponds to elastic behaviour which can be obtained for example from wire or tube of nickel-titanium from the drawing process.

Curve (2) corresponds to super-elastic behaviour which can be obtained for example from wire or tube of nickel-titanium from the drawing process to which thermo-mechanical treatment is applied.

Curve (3) corresponds to elasto-plastic behaviour which is conventional for numerous materials.

The slope of these curves and the value of the « plateaux » which can be observed for curves (2) and (3) can be modulated by applying heat or thermo-mechanical treatment to the material.

It is hence possible to impart different local behaviours to portions 12 and 21 of the needle and the insert so that movement of the insert inside the needle allows modification of deformation and hence of the pathway of said needle.

For example the behaviour of the curved portion 21 of the insert is of type (1) or (2) in the range of laws of behaviour illustrated in FIG. 3.

The behaviour of region 12 of the needle is one of behaviours of type (1), (2) or (3) illustrated in FIG. 3.

Figure 4:
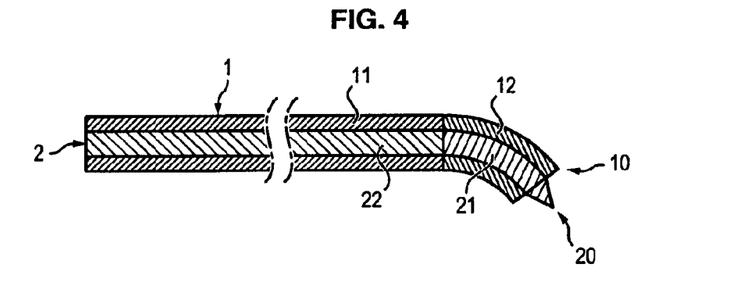
FIG. 4 is a cross-sectional view of a second embodiment of the invention.

FIG. 4 illustrates another possible configuration of the needle and the insert.

In this case, the needle has a distal region 12 of smaller rigidity than the remainder 11 of the needle.

The insert has a curved distal portion 21.

In this example the needle is made in 316L steel, a material currently given frequent use for medical needles.

However, contrary to conventional needles, the region 12 has been subjected to localised annealing whilst the remainder 11 of the needle has not undergone any annealing.

The effect of this annealing is locally to reduce the rigidity of the needle.

Compared with a nickel-titanium alloy, 316L steel has the advantage of being less costly; on the other hand it tolerates much more limited elastic strain (about ten times less than strains tolerated by nickel-titanium alloys).

The insert is made in a similar nickel-titanium alloy to the one described in the preceding example.

The distal region 12 of the needle is less rigid than the curved portion 21 of the insert which means that it is curved when it surrounds said portion 21 of the insert.

Of course, other configurations can be defined for the different portions of the needle and the insert, and other elastic behaviours than those illustrated in FIGS. 1 to 2B and 4.

For example, the respective positions of the more rigid and less rigid portions of the needle and the insert may be different from those in the example illustrated in FIG. 1, depending on intended applications.

Also, the needle and the insert may have more than two regions exhibiting different behaviour.

Figure 5A:
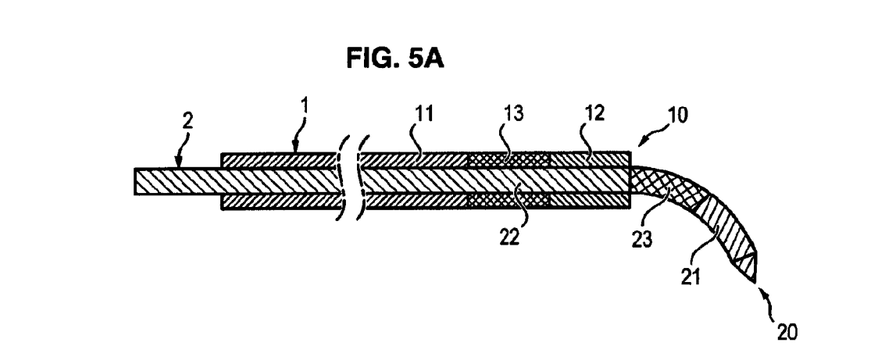
FIGS. 5A and 5B are cross-sectional views of a third embodiment of the invention, according to different relative positions of the needle and the insert.
Figure 5B:
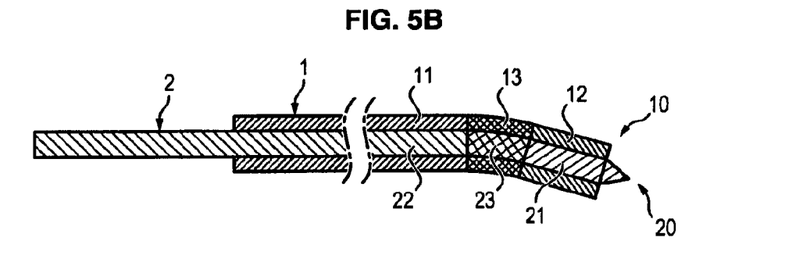

Said, non-limiting, embodiment is illustrated in FIGS. 5A and 5B.

In this example, the needle 1 has three regions 11, 12, 13 exhibiting different mechanical behaviour.

Compared with the needle illustrated in FIG. 1, the needle has a third region 13 located between region 11 and the distal region 12.

By means of suitable heat or thermo-mechanical treatment the region 13 has lesser rigidity than portion 12.

The insert 2 has three portions 21, 22, 23 exhibiting different mechanical behaviour.

Compared with the insert illustrated in FIG. 1, the insert has a third portion 23 located between the portion 22 and the distal portion 21.

With suitable heat or thermo-mechanical treatment the portion 23 obtains greater rigidity than portion 21.

As can be seen in FIG. 5A, the portions 23 and 21 are curved in a free condition (i.e. they project beyond the distal tip 10 of the needle 1).

Also, the regions 13 and 12 of the needle respectively have a length that is substantially equal to the length of portions 23 and 21.

When the insert 2 is retracted inside the needle 1 (as illustrated in FIG. 5B), the portions 23 and 21 of the insert are respectively surrounded by the regions 13 and 12 of the needle.

On account of the different behaviour of these different regions, the region 13 of the needle becomes curved (to a lesser extent than the portion 23 in a free condition), whilst region 12 remains straight.

The practitioner is therefore able to curve locally the needle at a certain distance from its distal tip, whilst keeping straight a distal portion of the needle.

Figure 6A:
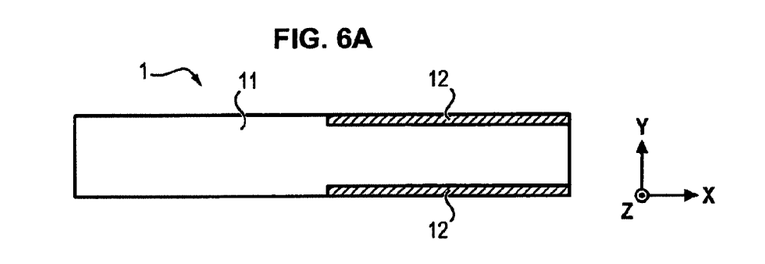
FIGS. 6A to 6C are profile, front and side views of a needle according to another embodiment.
Figure 6B:
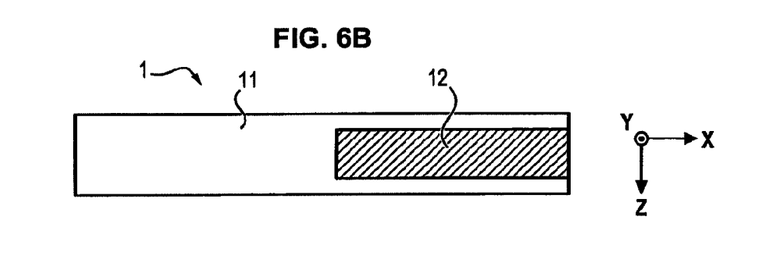
Figure 6C:
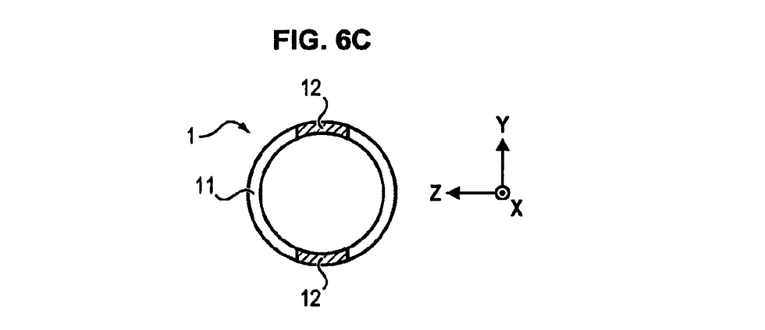

FIGS. 6A to 6C illustrate another embodiment of the needle, the needle being illustrated from a profile, overhead and side view respectively within an orthogonal reference frame x, y, z.

In this embodiment, two regions 12 having mechanical behaviour differing from the behaviour of the remainder 11 of the needle extend along two diametrically opposite generating lines of the needle.

Each of said regions 12 only extends over part of the circumference of the needle; the two regions 12 are therefore separated by two regions 11 which have the same mechanical behaviour as the remainder of the needle.

For example, the regions 12 are formed by heat treatment having the effect of locally reducing the rigidity of the needle.

Figure 7:
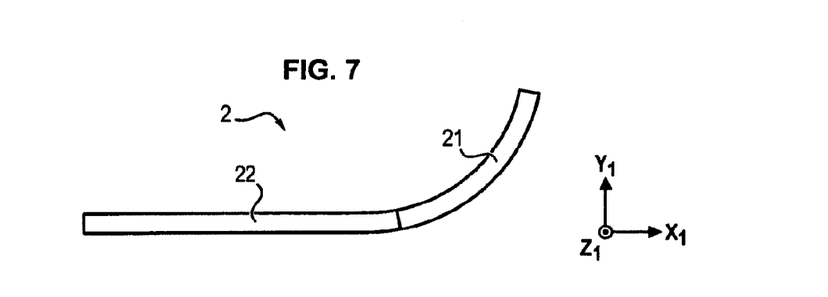
FIG. 7 is a profile view of an insert for guiding the needle illustrated in FIGS. 6A to 6C.

The insert 2 is shown in a free condition in FIG. 7 within an orthogonal reference frame x1, y1, z1, the rectilinear portion 22 of the insert extending in the direction of axis x1 and the curved portion 21 of the insert extending along the plane (x1, y1).

The curve of the insert can therefore be defined by the coordinates of the ends of the curved portion 21 along plane (x1, y1).

Figure 8:
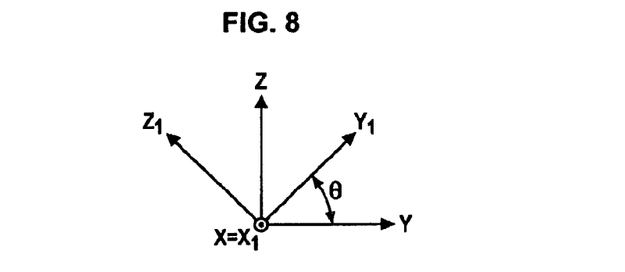
FIG. 8 illustrates the respective angle positions of the needle and the insert.

When the insert is inserted in the needle, the reference points (x, y, z) of the needle and (x1, y1, z1) of the insert have a common longitudinal axis (x=x1), and the two other axes can be offset by an angle θ, as illustrated in FIG. 8.

Since the mechanical behaviour of the needle is not homogeneous over the entire circumference of its distal portion, it is possible to obtain a different curve of the needle by varying the angle position θ of the curved portion 21 of the insert in relation to the needle.

Figure 9A:
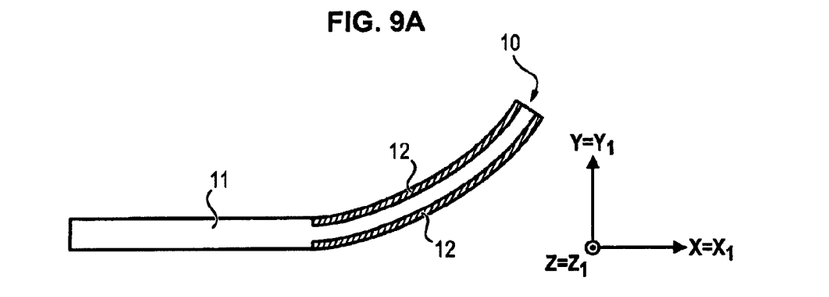
FIGS. 9A and 9B illustrate two different curves able to be obtained with the needle in FIGS. 6A to 6C and the insert in FIG. 7.

Therefore, as illustrated in FIG. 9A, if the axes y of the needle and y1 of the insert are aligned (i.e. θ=0°), a relatively pronounced curve of the needle is obtained although its radius of curvature is smaller than that of the curved portion of the insert in a free condition.

The curve of the curved portion 21 of the insert lies in the same plane as the less rigid regions 12 of the needle, which promotes localised deformation of the needle.

Figure 9B:
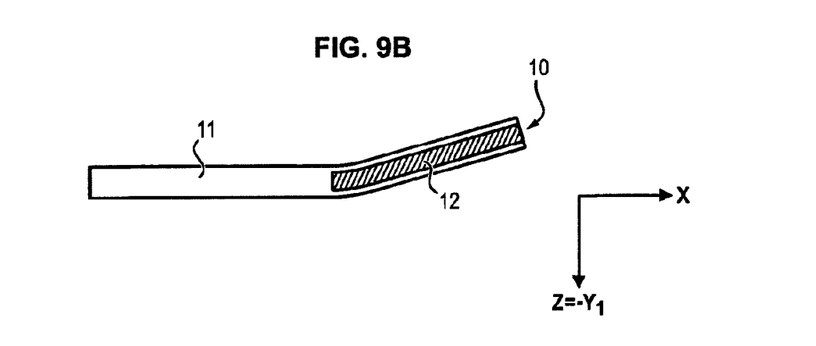

On the other hand, as illustrated in FIG. 9B, if the axes y of the needle and y1 of the insert are caused to be perpendicular (i.e. θ=−90°), a less pronounced curve of the needle is obtained than in the case shown FIG. 9A.

The curve of the curved portion 21 of the insert extends along the same plane as the regions 11 which have the same mechanical behaviour as the remainder of the needle, and which are more rigid than the regions 12.

It is specified that the FIGS. 9A and 9B illustrate the situation in which the insert is fully inserted in the needle, the distal ends of the needle and of the insert being aligned.

Depending on the position of the distal end of the insert relative to the position of the distal tip of the needle, it is therefore possible to obtain even more radii of curvature of the needle and the insert.

It will therefore be understood that by choosing different behaviours for different regions of the needle and the insert, and by choosing the length and position of these different regions, it is possible to obtain needles whose pathway can be modified by adjusting the axial position of the insert inside the needle.

Finally, although a nickel-titanium alloy lends itself particularly well to the implementation of the invention, the needle and the insert may be in any biocompatible material lending itself to heat or thermo-mechanical treatment allowing localised modification of the properties, and in particular the mechanical behaviour, of the needle and the insert.

In general materials are chosen that are elastic, elasto-plastic or super-elastic at the temperature of the human body.

Preferably, a material is chosen having sufficient elasticity to allow the needle to follow different curved pathways whilst being able to return to its initial shape.

Method for Manufacturing the Device

A description will now be given of a preferred method for manufacturing the device just described.

Localised heat or thermo-mechanical treatment is applied to the needle and/or insert to form regions having different behaviour in the needle and/or insert.

With said treatment it is possible to cause a local variation in the mechanical behaviour of the needle without modifying the thickness of the needle, this thickness remaining constant over its entire length. The same applies to the insert.

Figure 10:
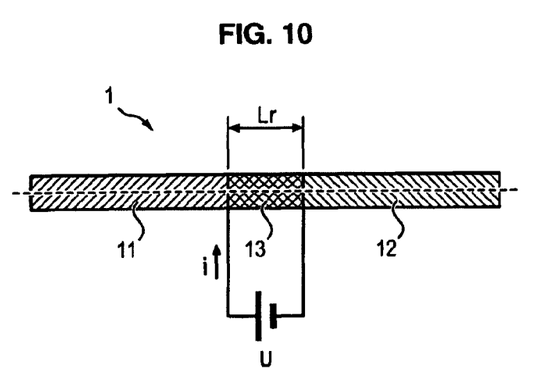
FIG. 10 schematically illustrates the conducting of localised heat treatment on the needle.
Figure 11:
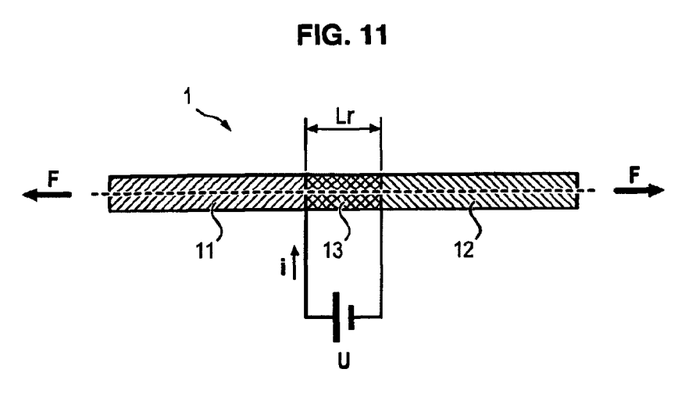
FIG. 11 schematically illustrates the conducting of thermo-mechanical treatment on the needle.

FIGS. 10 and 11 schematically illustrate local heat treatment and thermo-mechanical treatment respectively applied to the needle 1 via Joule effect.

With reference to FIG. 10, a voltage U is applied to the terminal ends of a portion 13 of the needle 1.

Since the needle is in an electrically conductive material, a current i passes through the portion 13 which is heated under Joule effect thereby modifying its elastic properties.

With reference to FIG. 11, the treatment in FIG. 6 is completed by applying a tensile stress to the ends of the needle, schematised by arrows F.

The application of this stress combined with the heat treatment allows the properties of portion 13 to be modified over its entire circumference.

The elastic behaviour of the portion 13 thus treated is dependent on treatment time, applied voltage, the length Lr of the treated region and the mechanical stress optionally applied.

The curved portion 21 of the insert can be obtained using a so-called « shape setting », process i.e. by imposing the desired shape on the material then performing adapted heat treatment.

For conducting of thermo-mechanical treatment, reference can be made to the article by D. Favier et al., "Influence of Thermomechanical processing on the superelastic properties of a Ni-rich Nitinol shape memory alloy", Materials Sciences and Engineering, A429 (2006), which describes thermo-mechanical treatment of a whole part.

Of course, any other process can be used which allows localised heat or thermo-mechanical treatment of the needle and/or insert.

Mention can be made of laser treatment for example, or induction heating.

Laser treatment is particularly advantageous for modifying the mechanical behaviour of the needle over only one part of the circumference of its distal portion.

This treatment allows controlled modification of the mechanical behaviour of a region extending over a determined angular sector of the circumference of the needle, without modifying the mechanical behaviour of a region extending over another angular sector of the circumference, the behaviour of this region then possibly being substantially identical to that of the remainder of the needle.

This localised laser treatment particularly allows the needle to be obtained that is illustrated in FIGS. 6A to 6C.

With thermo-mechanical treatment, the stress applied to the needle or insert may be tensile stress or radial stress . . . .

Preferably the heat and/or thermo-mechanical treatment is conducted in a neutral atmosphere to prevent any oxidation of the needle or insert materials.

Use of the Guiding Device

For use of the needle guiding device, the insert is inserted in the needle so as to obtain the desired curve at the distal portion of the needle.

When inserting the needle through the tissues, the practitioner actuates the insert in translation and/or rotation inside the needle so as to adapt the curve of the distal tip of the needle in relation to any obstacles encountered and to adapt its position in relation to the target.

In particularly advantageous manner the needle can be provided with sensors which allow real-time determination of the needle's curve.

REFERENCES

Webster et al., "Nonhlonmic modeling of needle steering", International Journal of Robotics Research, Sage Publications Ltd, 2006, 25, pp. 509-525

WO 2010/020591

US 2009/0270676

T. R. Wedlick et al., "Characterization of Pre-Curved Needles for Steering in Tissue", $31^{st}$ Annual International Conference of the IEEE EMBS Minneapolis, 26 Sep. 2009

P. Sears et al., "A steerable Needle Technology Using Curved Concentric Tubes", Proceedings of the 2006 IEEE/RSJ International Conference on Intelligent Robots and Systems, Oct. 9-15, 2006, pp. 2850-2856

D. Favier et al., "Influence of Thermomechanical processing on the superelastic properties of a Ni-rich Nitinol shape memory alloy", Materials Sciences and Engineering, A429 (2006)

The invention claimed is:

1. A device for guiding a medical needle, comprising said medical needle and an insert arranged slidably in translation and rotation inside the needle, wherein:

the insert, in a free condition, has a curved distal portion and the needle has at least a first region and a second region having different mechanical behaviour from a third region, the first and second regions extending along diametrically opposite generating lines of the needle over parts of the circumference of the needle, the third region extending along a generating line of the needle over a part of the circumference of the needle between the first and second regions, the mechanical behaviour of each of said first, second and third regions and of the curved distal portion of the insert being chosen so that a selected at least one of angular and longitudinal movement of the curved distal portion of the insert relative to the first and second regions of the needle causes localised deformation of at least one of the needle and the insert, depending on the angular position of the curved portion of the insert relative to said first and second regions of the needle.

2. The device of claim 1, wherein the needle has at least two regions of different rigidity, at least one of said regions having greater rigidity than the curved portion of the insert.

3. The device of claim 1, wherein said first, second, and third regions are adjacent over the circumference of the distal portion of the needle.

4. The device of claim 1, wherein the insert has a solid cylindrical shape of circular cross-section.

5. The device of claim 1, wherein the needle and the insert are in biocompatible metals that are elastic, elasto-plastic or super-elastic at the temperature of the human body.

6. The device of claim 5, wherein the needle and/or the insert are in nickel-titanium alloy.

7. The device of claim 1, wherein the needle and the insert are of constant thickness.

8. The device of claim 1, wherein the outer diameter of the needle is between 0.3 and 2 mm and the diameter of the insert is between 0.1 and 1.8 mm.

9. The device of claim 1, wherein the needle has, from its distal tip to its proximal end, a first portion having greater rigidity than the rigidity of the curved portion of the insert, and a second portion having smaller rigidity than the curved portion of the insert.

10. The device of claim 1, wherein the mechanical behaviour of at least one of the first, second and third regions of the needle is obtained by a thermal or thermo-mechanical treatment of the needle.

11. The device of claim 1, wherein the needle has a constant thickness and diameter.

* * * * *